United States Patent [19]

Hayes et al.

[11] Patent Number: 4,705,519
[45] Date of Patent: Nov. 10, 1987

[54] REPAIR MATERIAL FOR USE WITH BONES

[75] Inventors: William V. Hayes, Bandera; Turner, Albert H., Houston, both of Tex.

[73] Assignee: Hayes Separation, Inc., Bandera, Tex.

[21] Appl. No.: 896,885

[22] Filed: Aug. 15, 1986

Related U.S. Application Data

[62] Division of Ser. No. 706,138, Feb. 27, 1985, Pat. No. 4,643,735.

[51] Int. Cl.$^4$ ............................ A61F 2/28; A61K 6/08
[52] U.S. Cl. ........................................ 623/16; 623/66; 523/116; 525/903; 525/937
[58] Field of Search ............................ 623/16, 66, 11; 128/92 R, 924 J, 92 V, 92 P; 523/115, 116; 525/903, 937

[56] References Cited

U.S. PATENT DOCUMENTS

| 4,396,476 | 8/1983 | Roemer ............................ 523/115 X |
| 4,404,327 | 9/1983 | Crugnola et al. ............... 523/115 X |
| 4,535,485 | 8/1985 | Ashman et al. ........................ 623/16 |
| 4,554,727 | 11/1985 | Deckman et al. .................... 29/572 |

Primary Examiner—Richard J. Apley
Assistant Examiner—Alan W. Cannon
Attorney, Agent, or Firm—Gunn, Lee & Jackson

[57] ABSTRACT

A repair material enabling regrowth of damaged bones is set forth. In the preferred and illustrated embodiment, the repair material is polydivinylbenzene in particulate form. The particles are typically random sizes in a specified range, relatively porous, having a relatively high surface area per unit weight, thereby enabling bone growth supported by such particles.

2 Claims, No Drawings

REPAIR MATERIAL FOR USE WITH BONES

This is a divisional of application Ser. No. 06/706,138 filed Feb. 27, 1985, now U.S. Pat. No. 4,643,735.

BACKGROUND OF THE DISCLOSURE

The disclosed invention is a particulate material which aids and assists recovery from trauma to bones. Consider two or three examples which set forth the context in which the material is used. As one example, asume that a bone has been partially broken away. The material of this disclosure enables the bone to be filled with the material wherein subsequent bone growth occurs in the process of integrating the particulate material into the bone. As another example, the material can be used to fill an extraction socket to prevent bone resorption. This can be true whether the extraction socket results from partial or complete removal of the tooth that was previously there. Moreover, the material can be used to pack into a minor bone defect or in filling a portion of a bone removed by injury or as a result of disease.

Consider as another possibility the use of the present material in bone repair or replacement. This is particularly important for bones which have not been merely fractured but which have been shattered into multiple pieces. In particularly violent accidents, there is a possibility of bone shattering i.e., when the bone is broken into many pieces or chips. When the orthopaedic repair process is initiated, the bone which has been shattered into multiple chips and pieces may require substantial remedial repair which initially begins with locating some or all the bone chips to reposition them for the repair. This is difficult, and sometimes impossible. In some accidents, the bone chips simply cannot be located. Repositioning a multiplicity of randomly shaped retrieved bone chips may be difficult. For instance, in shattering accidents, some of the chips may be so badly displaced or lost that it is impossible to reposition all the bone chips as a preliminary step to repair of the injury. Imagine as an example that a shattering injury occurs to the tibia whereupon certain of the chips in the central portion of the tibia are missing. At the time of reconstruction, it is helpful to reposition the bone chips (to the degree they are available) so that the repaired tibia has the same length (upon healing) as before the injury. In the absence of such bone chips, the healing process hopefully involves a growing together of the two ends of the bone to span such chips as can be found. This is not necessarily an assured healing process. Moreover, it also requires that the bone chips be held in a substantially prealigned position in advance of the completion of the healing process; this also is somewhat chancy, and may well involve undue optimism in the positioning of the chips and the holding of that position, sometimes for weeks or months, as the healing process continues. So to speak, the remaining ends of the bone and the chips spanning the space between the ends of the bone must knit together ultimately to provide a healed bone. During the interim, some of the chips may be "floating" in position hopefully to be assimilated by the healing process. This requires excessively long immobilization of the limb, all to the inconvenience of the patient.

This disclosure is directed to a particulate material which can be used in bone repair. Assume in the foregoing example that the tibia is fractured in such a way as to be missing bone chips in a span of six or eight centimeters (for an adult). The healing process contemplated using the material of this disclosure then involves positioning the two ends of the tibia at the necessary spacing for healing to full length. Moreover, a few of the bone chips may be located and placed in the gap. To the degree that the chips cannot be found, the voids and cavities left in the reassembled chips are filled with the particulate material of this disclosure. Moreover, adjacent chips are reassembled with the particulate material of this disclosure between chips to enhance regrowth in the healing process. The material of this disclosure is integrated into the healed bone structure so that the chips grow together, even growing through the material of this disclosure. To this end, the repair material set forth below is porous to enable bone to grow through the material. Healing is thereby accelerated because there is no gap between adjacent chips. Moreover, healing appears to be accelerated with less discomfort to the patient, this being achieved through reduced immobilization.

Additionally, the healing process appears to be enhanced because the region of the healed bone involving the particulate material appears stronger. That is, it is stronger in that it is a composite of a bone (substantially calcium) and includes a supportive connected matrix of the particulate material of this disclosure. In that sense, the composite structure appears much stronger.

The present material is inert and does not appear to trigger rejection mechanisms. That is, the material is inert and remains in location, in tact, all during the healing process and is thus structurally integrated in the complete bone. Thus, it is described as free of body rejection mechanisms. The material is inert to the calcium deposited by the body in the healing process. That is, the calcium which knits the injured bone into a healed structure assimilates this material whereby the completed structure is enhanced in strength where joinder has occurred. The growth appears normal in the sense that the bone grows (heals) in the conventional fashion. When the healing process is completed, to the extent that any of the particulate material of this disclosure is located in the region where the bone marrow once was, that portion will simply comprise bone marrow having this material comingled therein.

BRIEF SUMMARY

The present bone repair material is described in general terms as an irregular polymer in substantially pure form, specifically polydivinylbenzene (PDVB hereafter) being formed in substantially irregular size and shape to enhance the grip and contact between the knitted bone and the particulate material. It is apparently porous, having particles in a specified range between maximum and minimum sizes, and has substantial surface area to enable more intimate contact in the bone.

DETAILED DESCRIPTION OF THE PREFERRED EMBODIMENT

The monomer divinylbenzene is available as ortho, meta and para isomers. Any of the three isomeric forms will suffice. Through techniques known in the art, the monomer is converted into the polymer which is described hereinafter as PDVB. It is polymerized to obtain an essentially pure polymer. Rather than straight chains, a substantial amount of irregular or random cross linking occurs. Because of this, and particularly because the benzene ring is integrated at multiple locations in the cross linked molecule, the material enables a product to be formed which is substantially porous, and which has a relatively high surface area per unit weight and which is otherwise chemically stable. The product of this disclosure is therefore preferably pure and is essentially free of traces of the monomer, catalyst, etc. The completed product is therefore a particulate material. The typical weight is about 0.4 grams per cc. The range is about 0.3 to about 0.45 grams per cc. The material is relatively porous and thus has a surface area which is optimum at about 500 square meters per gram. The range is about 150 to about 750 square meters per gram. As will be observed from the relatively light bulk density and the high surface area per unit weight, the material is relatively porous. The "pores" in the individual particles are a random shape, size and distribution. The material thus formed preferably has random particle size, shape and distribution. It is preferably screened to obtain particles in a range from perhaps 60 mesh on up to about 3/16 maximum particle length. Because there is a sense of randomness in this, and moreover since the particles are random in shape as well as size, this yields a material which particularly enhances bone knitting during the healing process as will be described.

The present disclosure contemplates the use of a mix of particles as mentioned above ranging from a maximum dimension of about 3/16 inch down to about 60 mesh. While this range of sizes might be used for large bone repairs, smaller particles within this range suffice for smaller repairs. That is, smaller repairs simply do not have room for such large particles.

For the foregoing reasons, this disclosure is particularly directed to a process of bone repair. Consider the following example as it relates to bone repair.

In a domestic cat, a hole was drilled in the bone of about ⅜ inch diameter and ⅜ inch depth. The hole penetrated the bone and exposed the bone marrow. A small portion of bone marrow was removed around the area of the drilled hole. The particulate material of this disclosure was then packed in the drilled hole. It was packed and tamped but no special packing effort was made other than packing the hole. Additionally, particulate material was deposited on the bone area around the hole, whereupon the incision providing access to the bone was subsequently sutured. After about six weeks of healing, the bone was removed from the cat and sectional cuts were made through the bone both near and across the drilled hole in the bone. The sectional cuts showed that the bone marrow, which has a jelly-like consistency, had comingled with the particulate material at the hole area. It appeared that the bone marrow function was thus sustained even though a portion of it had been removed at the hole. The bone marrow function was observed to continue on both sides of the hole and in the hole area so that it can be reasonably described as one continuous bone marrow. With regard to the bone structure, the calcium deposited during the healing process closed over a substantial portion of the hole and appeared to be closing over the hole completely. That is, the particles that were in the hole became integrated into the bone by means of the calcium deposited in that region such that the previously sharply defined drilled hole was much smaller and could not so readily be observed after the healing process had been partially (but no completely) completed. It was further noted that the bone was stronger in the region where the particulate material was located that it was at regions where no trauma had occurred. Last of all, it was observed that the particles deposited on the surface of the bone at and near the traumatized area were integrated into the bone by means of subsequently deposited calcium which thereby enhanced the strength of the bone.

The bone can thus be described as healing in the ordinary course of the healing process and yet the bone during the transition state between injury and healing and also upon completion of healing is made much stronger by incorporation of the particulate material in the vicinity. This particularly finds use where the injury leaves multiple irregular fragments. For instance, some of the fragments may well be impossible to locate after traumatic injury. The bone is thus "reassembled" at the requisite length or size and the missing chips are replaced with the particulate material of this disclosure. At the time of reassembly of the traumatized bone including chips, the chips are to a degree repositioned in physical alignment with the desired ultimate shape, size and profile of the healed bone and all spaces or gaps are filled with the particulate material of this disclosure. In fact, the thickness or diameter of the bone can be built up slightly by adding more of the particulate material of this disclosure so that the ultimate size or diameter of the bone is enlarged slightly. This enhances the strength engendered by the healing process. Moreover, it appears that there is a mesure of increased healing speed as a result of the particulate material which is included with the bone chips to obtain more rapid healing. Last of all, there appears to be accelerated healing because healing appears to occur in a more generalized region rather than from the facing free ends of a fractured bone wherein it is hoped that the two ends "grow together" thereby knitting to form a healed bone.

Tissue rejection appears to be nil. Compatability of the particulate material with the bone appears to be quite desirable and enhances the healed bone by providing added strength without interferring with the bone marrow reconstruction in the healing process.

While the foregoing is directed to the preferred embodiment of the present invention, other and further embodiments of the invention may be devised without departing from the basic scope thereof, and the scope thereof is determined by the claims which follow.

What is claimed is:

1. A composition of matter for repairing an injured bone in a body comprising substantially pure, randomly cross linked polydivinyl benzene in particulate form, essentially free of monomer and catalyst, and which particulate composition enables bone knitting such that the particulate is integrated into the healed bone upon completion of the healing process wherein the composition has a surface area of 150 square meters per gram or more and a weight of about 0.3 to 0.45 gm/cc to linked monomer or polymer having sufficient cross linking to form an irregular shape with pores, the porous particulate composition defining an inert matrix enabling bone growth therewith.

2. The composition of matter of claim 1 wherein the particulate material has a minimum surface area of at least about 150 square meters per gram and is a mix of particle sizes where some of the particles have at least 500 square meters per gram surface area, and wherein the density is about 0.4 grams per cubic centimeter.

* * * * *

UNITED STATES PATENT AND TRADEMARK OFFICE
CERTIFICATE OF CORRECTION

PATENT NO.    :   4,705,519
DATED         :   November 10, 1987
INVENTOR(S)   :   William V. Hayes, et al It is certified that error appears in the above-identified patent and that said Letters Patent is hereby corrected as shown below:

| | |
|---|---|
| Col. 2, line 30 | 'in tact" should read --intact--. |
| Col. 3, line 66 | "no" should read --not--. |
| Col. 4, line 1  | "that" should read --than--. |
| Col. 4, line 50 | "polydivinyl benzene" should read --polydivinylbenzene--. |
| Col. 4, line 56 | "to" should read --of--. |

Signed and Sealed this

First Day of November, 1988

Attest:

DONALD J. QUIGG

Attesting Officer

Commissioner of Patents and Trademarks